United States Patent [19]

Kamiyama et al.

[11] 4,354,961
[45] Oct. 19, 1982

[54] METHOD OF PREPARING A CATALYST FOR SYNTHESIZING UNSATURATED ESTERS

[75] Inventors: Setsuo Kamiyama, Kawagoe; Kouji Shiozawa, Hatoyama; Eiichiro Nishikawa; Katsumi Kaneko, both of Ooi, all of Japan

[73] Assignee: Toa Nenryo Kogyo Kabushiki Kaisha, Tokyo, Japan

[21] Appl. No.: 209,166

[22] Filed: Nov. 21, 1980

[30] Foreign Application Priority Data

Jan. 24, 1980 [JP] Japan .................... 55-6331

[51] Int. Cl.$^3$ .............. B01J 27/02; B01J 21/18; B01J 29/16; B01J 29/00
[52] U.S. Cl. .................... 252/439; 252/447; 252/456; 252/458; 252/459; 252/464
[58] Field of Search ............. 252/439, 447, 456, 458, 252/459, 464

[56] References Cited

U.S. PATENT DOCUMENTS

| | | | |
|---|---|---|---|
| 2,930,765 | 3/1960 | Cooper et al. | 252/447 X |
| 3,717,670 | 2/1973 | Schultz | 252/447 X |
| 3,755,423 | 8/1973 | Onodo et al. | 260/497 A |
| 3,875,048 | 4/1975 | Iwaisoko et al. | 208/139 |
| 3,876,694 | 4/1975 | Gaenzler et al. | 252/466 PT X |
| 3,993,598 | 11/1976 | Arey, Jr. et al. | 252/466 PT X |
| 4,020,011 | 4/1977 | Nishikawa | 252/441 |
| 4,020,012 | 4/1977 | Miura et al. | 252/441 |
| 4,288,347 | 9/1981 | Rabinovich et al. | 252/466 PT X |

FOREIGN PATENT DOCUMENTS

| | | | |
|---|---|---|---|
| 5522640 | 8/1978 | Japan | 252/447 |
| 54-146289 | 11/1979 | Japan | 252/439 |
| 54-14914 | 2/1979 | Japan . | |
| 388274 | 6/1965 | Switzerland . | |
| 1494430 | 12/1977 | United Kingdom . | |

Primary Examiner—Delbert E. Gantz
Assistant Examiner—William G. Wright
Attorney, Agent, or Firm—Rebecca Yablonsky

[57] ABSTRACT

A method of preparing a catalyst for the diacyloxylation of conjugated dienes such as butadiene by reaction with a carboxylic acid such as acetic acid and oxygen, which comprises separately and successively impregnating a carrier, for example carbon, with a solution of a Group VIII noble metal in a mixture of a mineral acid and an organic solvent, then with a solution of a Group IVA, VA or VIA element or compound thereof in an organic solvent.

4 Claims, 10 Drawing Figures

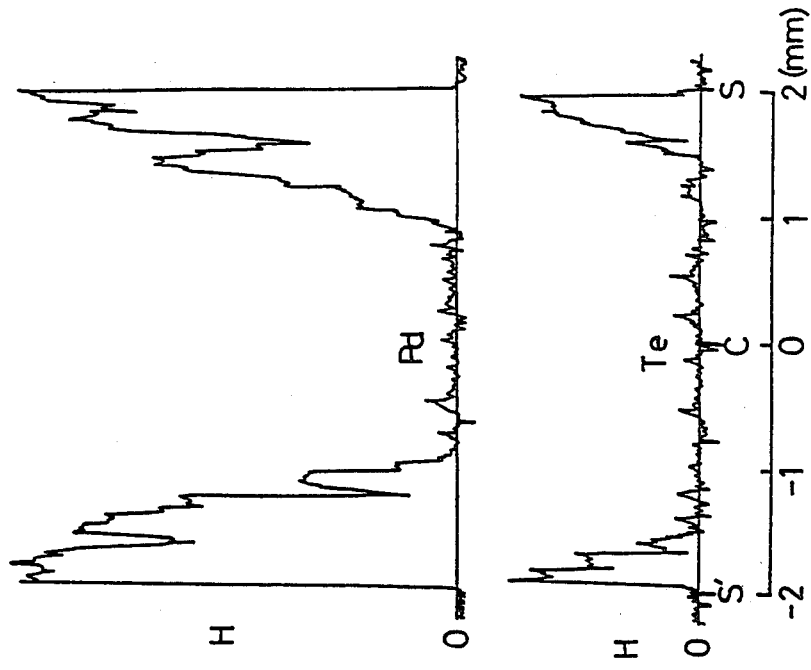
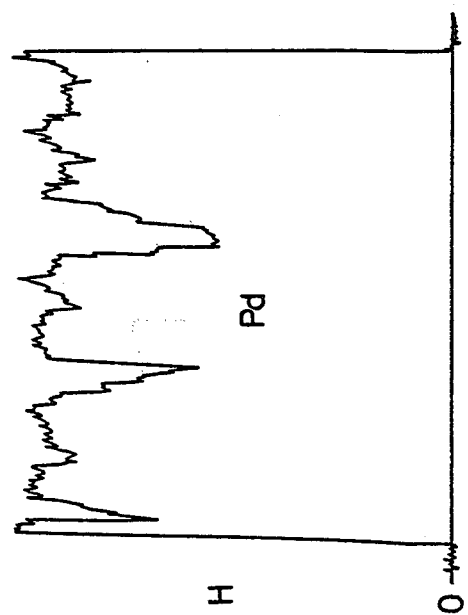

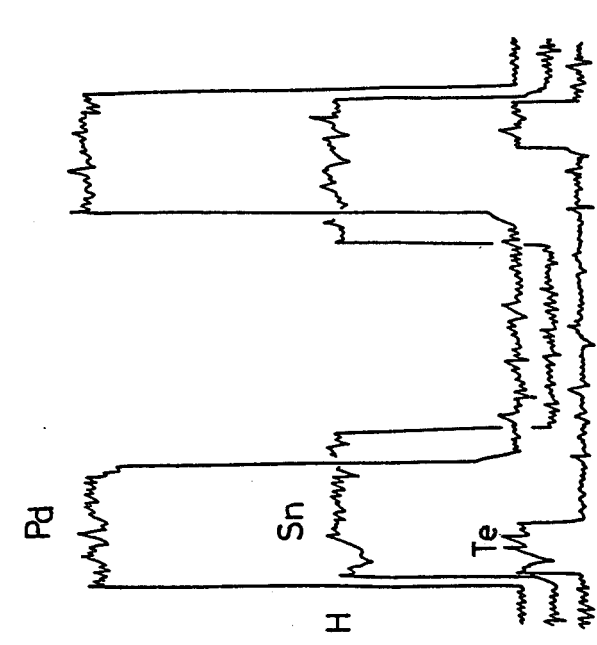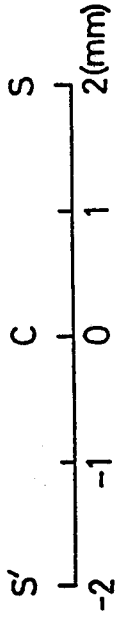
FIG. 4
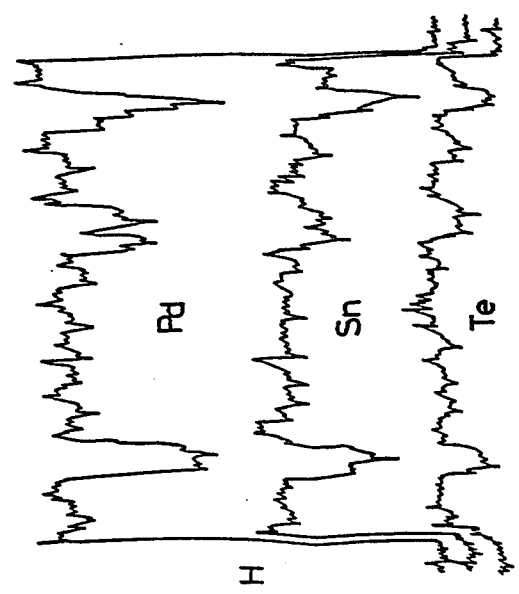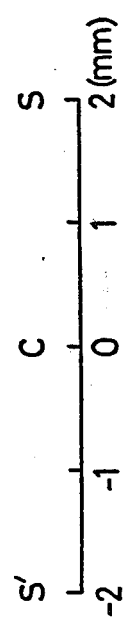
FIG. 5

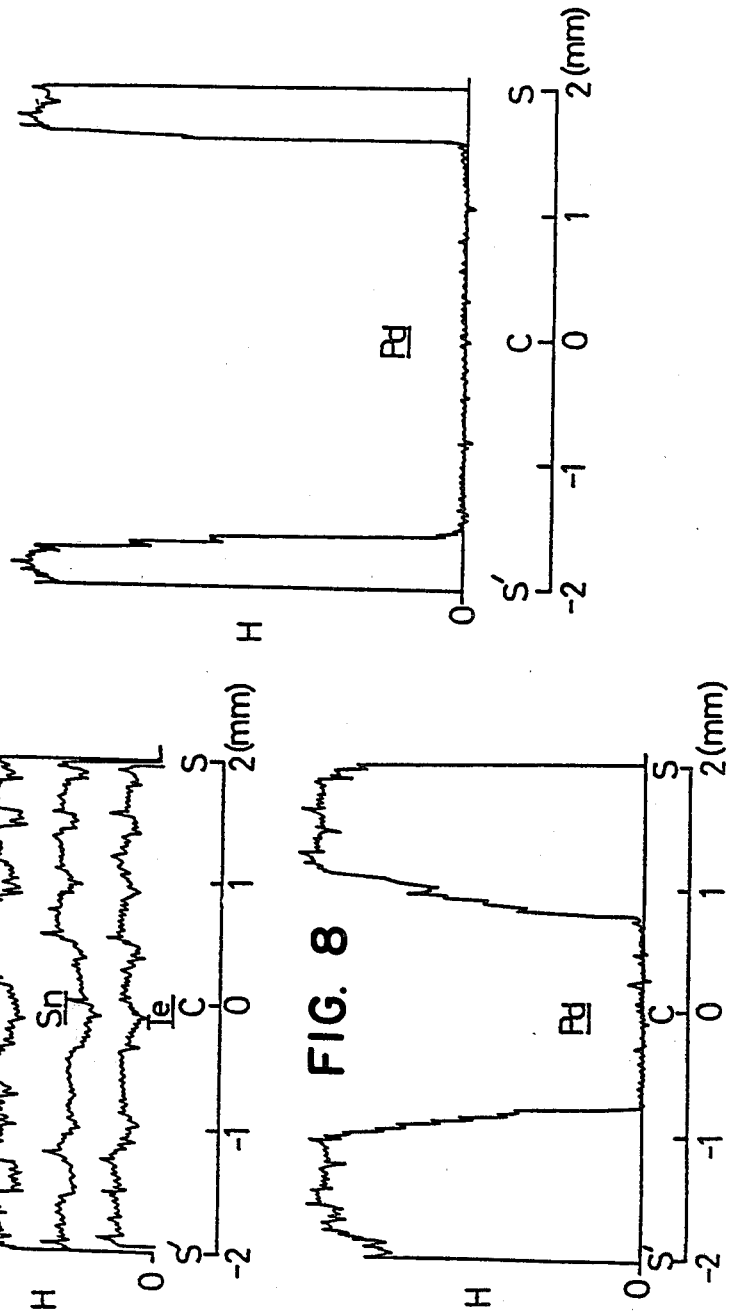

METHOD OF PREPARING A CATALYST FOR SYNTHESIZING UNSATURATED ESTERS

BACKGROUND OF THE INVENTION

This invention relates to a catalyst for use in the manufacture of unsaturated esters, particularly diacyloxyalkenes. More particularly, it is concerned with a solid catalyst for use in the manufacture of diacyloxyalkenes by reacting conjugated dienes, carboxylic acids and oxygen.

Diacyloxyalkenes are useful as raw materials for a variety of industrial applications. For example, 1,4-butanediol derived from 1,4-diacyloxybutene-2 is an industrially useful compound serving as a solvent, or an intermediate for the manufacture of tetrahydrofuran, γ-butyrolactone, polyesters, or the like.

It is known to manufacture diacyloxyalkenes by contacting a conjugated diene and oxygen with a catalyst composed of a Group VIII noble metal such as palladium and platinum, or a mixture of such a noble metal with selenium, tellurium, anitmony, bismuth, lead or the like in the presence of a carboxylic acid. For example, it has hitherto been proposed to manufacture 1,4-diacyloxy-2-butenes by contacting a conjugated diene, oxygen and a carboxylic acid with a catalyst composed of palladium, iridium, platinum, rhodium, ruthenium or the like, or a mixture of such a metal with copper, silver, zinc, nickel or the like as disclosed in Japanese Patent Publication No. 27290/1973, or to use a catalyst composed of a combination of palladium, and antimony, bismuth, selenium or tellurium as disclosed in Japanese Patent Application Laid-Open Specification No. 11812/1974.

Applicants have now found that the catalysts prepared by known methods do not have a sufficiently high activity because the metal component is not uniformly distributed on the carrier, and also because known multicomponent catalysts containing a plurality of metal components do not have a uniform distribution of each component on the carrier. Examples of such known catalysts include a catalyst obtained by dissolving a noble metal salt such as palladium chloride, and a salt of copper, zinc or the like in a mineral acid or acetic acid, incorporating a carrier into the resulting solution, and evaporating the mixture to dryness (Japanese Patent Publication No. 27290/1973); a catalyst obtained by treating with nitric acid activated carbon prepared by crushing coconut shells, incorporating the activated carbon into a hydrochloric acid solution containing palladium chloride, tellurium dioxide, selenium dioxide and antimony trichloride, and evaporating the solution to dryness (Japanese Patent Application Laid-Open Specification No. 11812/1974); a catalyst obtained by incorporating coconut shell activated carbon into an acetone solution of sulfur chloride, evaporating it to dryness, incorporating the evaporation product into an aqueous solution of hydrochloric acid containing palladium and niobium pentachloride, and evaporating the solution to dryness (Japanese Patent Application Laid-Open Specification No. 14914/1979), and a catalyst obtained by incorporating an ethanol solution of palladium acetate and activated carbon into a nitric acid solution of copper, and evaporating the mixed solution to dryness (Japanese Patent Application Laid-Open Specification No. 147189/1979).

All the known methods for preparing a catalyst by incorporating a carrier into a solution containing a catalytic component involve difficulty in achieving even distribution of the catalytic component from the surface of the catalyst to the interior thereof, and have a tendency to contain a smaller quantity of the catalytic component in the interior thereof. With a known catalyst containing a plurality of catalytic components, there is difficulty in maintaining the optimum proportions of the components throughout it, and different quantities of each component are contained in different parts thereof.

Applicants have therefore investigated a method which permits uniform distribution of the catalytic component or components on the carrier, and have discovered that it is possible to achieve uniform distribution of the or each catalytic component on the carrier if one uses a two-step impregnation method. That is to say, a noble metal belonging to Group VIII of the periodic table is supported on the carrier using a solution prepared by dissolving the metal compound in a mixture of an organic solvent and a mineral acid, and after washing, drying and calcining as may be needed, a compound of an element belonging to Group IV, V, or VI of the periodic table is supported on the obtained carrier containing the noble metal, using an organic solvent solution of the compound. This invention is based on this dicovery.

SUMMARY OF THE INVENTION

Thus, this invention consists essentially in a method of preparing a catalyst for use in the synthesis of unsaturated esters, particularly in the diacyloxylation of conjugated dienes, which comprises supporting on a carrier a compound of a least one noble metal selected from the group of noble metals belonging to Group VIII of the periodic table, in the form of a solution in an organic solvent containing a mineral acid, and further supporting on the carrier at least one element selected from the group of elements belonging to Groups, IV, V and VI, particularly Groups IVA, VA and VIA of the Fisher Scientific Company periodic table (excluding those of the second period), or a compound thereof in the form of a solution in an organic solvent.

BRIEF DESCRIPTION OF THE DRAWINGS

FIGS. 2 to 10 show the results of X-ray microanalysis for the distribution of the catalytic components in the catalysts prepared by the method of this invention and the method known in the art.

DETAILED DESCRIPTION

Figure 1:
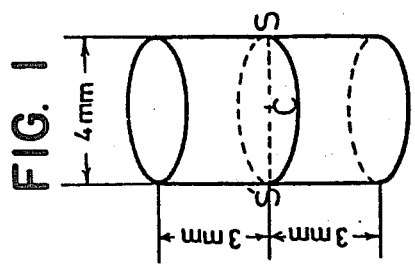
FIG. 1 is a perspective view illustrating the cross section in which the catalysts prepared as hereinabove described are cut for examination by an X-ray or electron beam microanalyzer.

Any carrier for a solid catalyst known in the art for use in the synthesis of diacyloxyalkenes from a conjugated diene, a carboxylic acid and oxygen may be employed as the carrier for the catalyst of this invention. Examples of the carrier include activated carbon, silica, alumina, silica-alumina, zirconia, thoria, clay, diatomaceous earth, bauxite, pumice and silicon carbide. it is desirable to use activated carbon, silica or alumina among others, and activated carbon is most preferred. The carrier may be pretreated by, for example, heating in the presence or absence of hydrochloric acid, nitric acid, or the like, though it is also possible to use it without any such pretreatment.

The noble metals of Group VIII of the periodic table from which the first component of the catalyst according to this invention is selected include palladium, platinum, ruthenium, rhodium, osmium and iridium. It is preferred to sue palladium or platinum and palladium is most preferred. The second component of the catalyst according to this invention may be selected from among the elements belonging to Groups IV, V and VI of the periodic table (excluding those of the second period), i.e., the Group IV, V and VI elements excluding carbon, nirogen and oxygen. It is preferred to employ tellurium, selenium, sulfur, antimony, bismuth, germanium, tin, lead and tellurium, selenium and tin are particularly preferred.

According to this invention, these noble metals and elements are usually used in the form of a solution in water or an organic solvent. They are usually used in the form of a compound which is soluble in water or an organic solvent, e.g., an inorganic salt such as a halide, nitrate, sulfate or carbonate, or an organic salt such as an acetate, oxalate or amine salt. It is, however, equally possible to use an element per se, an oxide thereof, or an element or compound thereof which is soluble in a mixture of an organic solvent and a mineral acid.

Examples of the compounds of the Group VIII noble metals and the Group IV, V and VI elements which are applicable for this invention include the following. Examples of the palladium compounds include palladium chloride, palladium nitrate, palladium sulfate and palladium oxide; examples of the platinum compounds include platinum dichloride, platinum tetrachloride, chloroplatinic acid and platinum oxide, and examples of the ruthenium compounds include ruthenium oxide, ruthenium dichloride, ruthenium tetrachloride, and ruthenium hydroxide. Examples of the rhodium compounds include rhodium chloride; examples of the osmium compounds include osmium tetrachloride, and examples of the iridium compounds include iridium tetrachloride and potassium iridate. Examples of the tellurium compounds include tellurium tetrachloride and tellurium dichloride; examples of the selenium compounds include selenic acid and selenium dioxide, and examples of the anitmony compounds include antimony trichloride and antimony pentachloride. Examples of the bismuth compounds include bismuth chloride and bismuth oxychloride; examples of the germanium compounds include germanium tetrachloride; examples of the tin compounds include tin dichloride, tin tetrachloride and tin acetate, and examples of the lead compounds include lead dichloride, lead chlorate and lead acetate.

Suitable organic solvents for the purpose of this invention are compounds containing oxygen, such as alcohols, ketones and ethers. Specific examples of the organic solvents include alcohols such as methanol, ethanol, isopropyl alcohol, isobutanol and normal butanol; ketones such as acetone, methyl ethyl ketone and methyl isobutyl ketone, and ethers such as ethyl ether, isopropyl ether, normal propyl ether, isobutyl ether and normal butyl ether. It is particularly preferred to use methanol, ethanol or acetone. These organic solvents may be used either individually, or in the form of a mixture thereof. It is also possible to use a mixture of such an organic solvent with a saturated hydrocarbon such as normal hexane, normal heptane, cyclohexane, benzene, toluene or xylene. The same or different organic solvents may be used for application of the first and second catalytic components to the carrier.

The mineral acid for use in the method of this invention may be selected from among hydrohalogenic acids, nitric acid, sulfuric acid, phosphoric acid, or the like. Hydrochloric acid and nitric acid are particularly preferred.

This invention relates to an improvement in the method of supporting the Group VIII noble metal and the Group IV, V, or VI element on the carrier. The improved method of this invention comprises two steps, i.e. supporting the Group VIII noble metal using a solution of a metal compound in an organic solvent containing a mineral acid, and then supporting the Group IV, V or VI element using a solution thereof in an organic solvent.

According to this invention, it is essential to conduct the aforementioned two steps in the order in which they have hereinabove been set forth, i.e., the first step of supporting the Group VIII noble metal on the carrier, and the second step of supporting the Group IV, V or VI element thereon. If the order is reversed, and the second step precedes the first step, the element applied to the carrier is dissolved during the application of the noble metal, resulting in failure of the Group VIII noble metal and the Group IV, V or VI element to be evenly distributed in the catalyst which is formed; therefore, the objects of this invention cannot be attained.

The first step of supporting the Group VIII noble metal on the carrier may be carried out by dissolving a compound of the metal in an organic solvent containing a mineral acid, and supporting the resulting solution on the carrier. More specifically, any method known in the art may be employed, but it is preferable to perform the application by immersing the carrier in the aforementioned solution to permit the carrier to adsorb the noble metal compound, removing the solvent by filtration or decantation, and drying the carrier, or drying or calcining it after washing if necessary.

It is necessary to select the concentration of the Group VIII noble metal in its soluion in an organic solvent containing a mineral acid to permit the application of the noble metal compound so that 0.01 to 10% by weight, and preferably 0.1 to 3% by weight, of the noble metal may be applied to the carrier. The concentration of the noble metal compound in the solution depends on the kind of the carrier material, its quantity, the time for which the carrier is immersed in the solution, the immersion temperature, or the like, but if activated carbon is used as the carrier, it is preferable that the solution contain 0.01 to 5 g of the noble metal compound per 100 g. The solution preferably contains a maximum of 0.2 gram mol of the mineral acid per 100 g, and a maximum of 20% by weight of water. The carrier and the solution preferably have a ratio of volume of 0.2 to 1:1. The immersion time may be in the range of 1 to 15 hours, preferably 3 to 10 hours. The immersion of the carrier in the solution is usually performed at room temperature, but may also be carried out under heat.

In order to conduct the second step of applying the Group IV, V and VI element, it is desirable to follow the same procedures as hereinabove set forth for the application of the Group VIII noble metal. It is necessary to select the concentration of the element in the solution thereof so that the carrier supporting thereon the noble metal applied during the first step, and immersed in the solution of the compound of the Group IV, V or VI element may contain 0.01 to 10% by weight, preferably 0.1 to 3% by weight, of the element or compound thereof in terms of the weight of the element, and 0.05 to 10 gram atoms of the element per gram atom of the Group VIII noble metal.

In order to achieve the application of the element in the aforementioned quantity, it is necessary to take into account the kind of the carrier material to be used, the kind of the noble metal involved, its quantity applied to the carrier, the quantity of the solution to be used, immersion time and temperature, and the like. If activated carbon is used as the carrier, it is desirable to ensure that 100 g of the solution contain 0.01 to 5 g of the compound of the element. The solution should preferably not contain more than 20% by weight of water. The ratio of the carrier to the solution, and the immersion time and temperature which have hereinbefore been set forth for the first step may appropriately be employed again for the second step.

The catalyst obtained by supporting on the carrier the compound of the Group VIII noble metal during the first step and the Group IV, V or VI element or its compound during the second step is dried or calcined, after it has been washed if necessary. The catalyst thus obtained is treated with hydrogen or a reducing oganic compound for reduction of its metal components to thereby provide a catalyst for use in the diacyloxylation of conjugated dienes.

The catalyst prepared as hereinabove described has a uniform distribution of the Group VIII noble metal and the Group IV, V and VI element in the interior of the carrier. Therefore, the catalyst can be advantageously used for the reaction of a conjugated diene, a carboxylic acid and oxygen to produce a higher yield of diacyloxyalkenes per unit weight of the noble metal than any known solid catalyst in which the carrier supports the catalytic component on its surface alone.

The invention will now be described in further detail with reference to the following examples.

EXAMPLE 1

10 g of molded activated carbon having a particle size of 4 mm in diameter and 6 mm in length were treated with 15% by weight of nitric acid by heating under reflux for six hours. Then the activated carbon was immersed in 40 ml of a first immersion solution prepared by dissolving 0.1750 g of palladium chloride ($PdCl_2$) and 3.3 ml of 12 N hydrochloric acid in 40 ml of acetone, and left to stand at room temperature for six hours while the solution was stirred from time to time.

Then the first immersion solution was removed by decantation, and the sediment was dried in the air at 120° C. for eight hours, whereby activated carbon carrying palladium chloride was obtained. The activated carbon was then immersed in 40 ml of a second immersion solution prepared by dissolving 0.0904 g of tellurium tetrachloride ($TeCl_4$) in 40 ml of methanol, and allowed to stand at room temperature for six hours. Then the second immersion solution was removed by decantation and after the sediment was dried in a stream of nitrogen at 150° C. for three hours, it was reduced with nitrogen saturated with methanol at room temperature by heating at 200° C. for three hours and 400° C. for two hours, whereby a catalyst for diacyloxylation (Catalyst A) was obtained.

This catalyst contained 0.95% by weight of palladium and 0.41% by weight of tellurium and had a tellurium/palladium atom ratio of 0.36. The palladium on the catalyst amounted to 90% of the palladium in the first immersion solution, and the tellurium thereon amounted to 95% of that in the second immersion solution. It is thus noted that the method of this invention permits the carrier to adsorb the catalytic components selectively from their respective solutions.

For the sake of comparison, Catalyst B was prepared in the following manner (Comparative Example 1). 10 g of molded activated carbon having a particle size of 4 mm in diameter and 6 mm in length were treated with 15% by weight of nitric acid by heating under reflux for six hours. The activated carbon was then immersed in a solution prepared by dissolving 0.1750 g of $PdCl_2$ and 0.0536 g of tellurium dioxide ($TeO_2$) in 40 ml of 6 N hydrochloric acid, and allowed to stand at room temperature for 24 hours.

The residual solution was removed by decantation and after the sediment was dried in the air at 120° C. for eight hours, it was dried in a stream of nitrogen at 150° C. for three hours and reduced with methanol at room temperature by heating at 200° C. for three hours and 400° C. for two hours, whereby Catalyst B for diacyloxylation was prepared. Catalyst B contained 0.95% by weight of palladium and 0.41% by weight of tellurium, and had a palladium/tellurium atom ratio of 0.36. The palladium on Catalyst B amounted to 80% of the palladium in $PdCl_2$ in its hydrochloric acid solution, and the tellurium thereon amounted to only 50% of that in the $TeO_2$.

As shown in FIG. 1, Catalysts A and B were each cut along the diametral cross section extending through its center, and the palladium and tellurium on the cross section were examined by an X-ray or electron beam microanalyzer measuring the L α-rays at 4.368 Å for palladium and at 3.289 Å for tellurium. The results are shown in FIG. 2 for Catalyst A, and FIG. 3 for Catalyst B. In each of FIGS. 2 and 3, the axis of abscissa indicates the cross-sectional line S'CS of the catalyst; C, the center of the catalyst; and S and S', the opposite outer surfaces of the catalyst, while the axis of ordinate indicates the X-ray intensity which is proportional to the quantity of the metals carried on the catalyst.

As is obvious from FIG. 2, the catalyst prepared by the method of this invention had a substantially uniform distribution of palladium and tellurium from the surfaces to the interior thereof. It will be noted, on the other hand, that Catalyst B prepared by the known method contained palladium only in an area not deeper than 1 mm below the carrier surfaces, and tellurium in an area not deeper than 0.5 mm, and virtually no palladium or tellurium in its center.

Catalysts A and B were employed by way of example for the synthesis of diacetoxybutenes from butadiene, acetic acid and oxygen.

4 g of each catalyst were placed in a stainless steel reaction tube having an inside diameter of 18 mm, and the reaction was conducted continuously at a temperature of 80° C. by feeding the reaction tube with glacial acetic acid at a rate of 12.5 ml per hour, butadiene at a rate of 60 millimols per hour and oxygen at a rate of 40 millimols per hour. Upon completion of five hours after the reaction was started, the space time yield of the diacetoxybutene formed, the efficiency of palladium, and the selectivity of the catalyst for 1,4-diacetoxybutene were examined as shown in Table 1 below. As is obvious from Table 1, the catalyst prepared by the method of this invention was found superior in both the space time yield and the palladium efficiency, to the catalyst according to the known method.

TABLE 1

| Catalyst | Space time yield (g/lit. cat./hr) | Palladium efficiency (mol/g atom/hr) | 1,4-Selectivity (%) |
| --- | --- | --- | --- |
| A | 125 | 19.8 | 92.3 |
| B | 71 | 10.2 | 92.4 |

EXAMPLE 2

Catalyst C composed of palladium, tellurium and tin was prepared by repeating the procedures of Example 1, except that 40 ml of a solution prepared by dissolving 0.0904 g of tellurium tetrachloride ($TeCl_4$) and 0.2185 g of tin tetrachloride ($SnCl_4$) in 40 ml of methanol were used instead of the methanol solution of tellurium tetrachloride, i.e., the second immersion solution in Example 1. The catalyst contained 0.95% by weight of palladium, 0.41% by weight of tellurium and 0.95% by weight of tin, and had a tellurium/palladium atom ratio of 0.36 and a tin/palladium atom ratio of 0.90.

For the sake of comparison, Catalyst D was prepared by repeating the procedures of Comparative Example 1, except for the use of a solution prepared by dissolving 0.1750 g of palladium chloride ($PdCl_2$), 0.0250 g of tellurium dioxide ($TeO_2$) and 0.2185 g of tin tetrachloride ($SnCl_4$) in 40 ml of 6 N hydrochloric acid. Catalyst D contained 0.95% by weight of palladium, 0.41% by weight of tellurium and 0.95% by weight of tin.

The distribution of each component of Catalysts C and D was determined by repeating the procedures of Example 1, and using the L $\alpha$-ray of 3.600 Å for tin. The results are shown in FIGS. 4 and 5, respectively. As is obvious from the results shown in FIGS. 4 and 5, Catalyst C of this invention (Example 2) showed a uniform distribution of its catalytic components, while Catalyst D (Comparative Example 2) contained palladium only in an area not deeper than 1 mm below its outer surface, and tin only in an area not deeper than 1.25 mm.

Then Catalysts C and D were tested for the synthesis of diacetoxybutenes by repeating the procedures described in Example 1. The results are shown in Table 2. As the results shown therein make clear, Catalyst C of this invention was found superior to Comparative Catalyst D both in space time yield and in palladium efficiency.

TABLE 2

| Catalyst | Space time yield (g/lit. cat/hr) | Palladium efficiency (mol/g atom/hr) | 1,4-Selectivity (%) |
| --- | --- | --- | --- |
| C | 205 | 32.7 | 91.7 |
| D | 103 | 14.7 | 91.9 |

EXAMPLE 3

Catalyst E was prepared by repeating the procedures of Example 1, except that the quantity of the 12 N hydrochloric acid was reduced to 1.7 ml (i.e., forming a mixed solution of 0.5 N hydrochloric acid and acetone), and the distribution of each of its components was likewise measured. The results are shown in FIG. 6. It will be noted from FIG. 6 that Catalyst E had a uniform distribution of palladium.

COMPARATIVE EXAMPLES 3 TO 5

Examination was made of the effect of variation in the concentration of hydrochloric acid in the known method employing an aqueous solution of hydrochloric acid.

Figure 9:
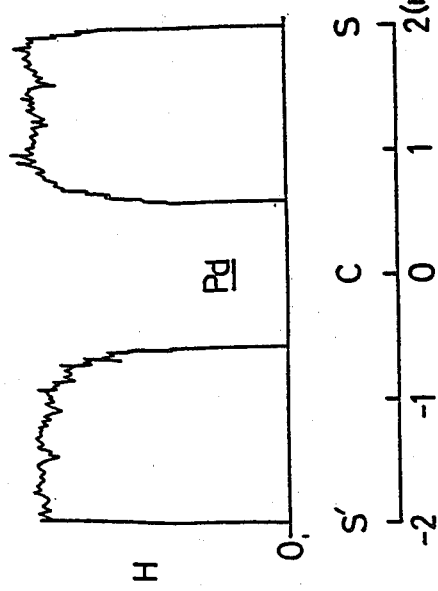

Catalyst F (Comparative Example 3) carrying only palladium was prepared by immersing the carrier in a solution obtained by dissolving 0.1750 g of palladium chloride ($PdCl_2$) in 40 ml of 0.1 N hydrochloric acid, and the distribution of palladium therein was examined. Likewise, Catalyst G (Comparative Example 4) and Catalyst H (Comparative Example 5) were prepared by using 6 N and 12 N hydrochloric acid, respectively, and the palladium distribution of each catalyst was examined. The results for Comparative Examples 3 to 5 are shown in FIGS. 7 to 9, respectively. It will be noted from FIGS. 7 to 9 that none of these catalysts contained palladium in its center, though the area containing palladium approached the center of the catalyst with an increase in the concentration of hydrochloric acid.

On the other hand, the method of this invention provides a catalyst having an even distribution of palladium, even if 0.5 N hydrochloric acid is used, as attested by Example 3.

COMPARATIVE EXAMPLE 6

Figure 10:
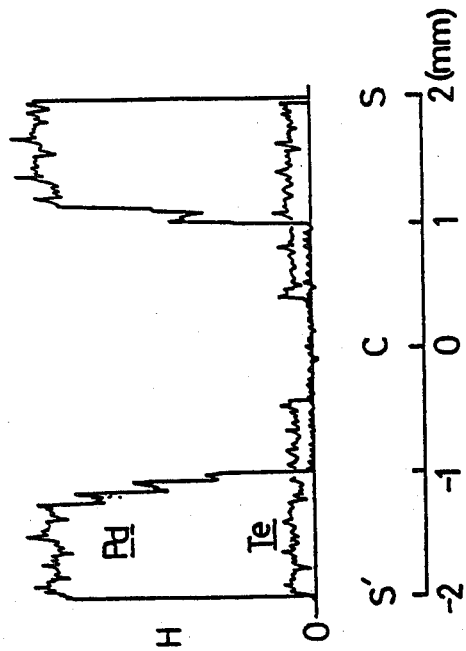

Activated carbon as used in Example 1 was immersed in a mixed solution obtained by mixing the first immersion solution (solution of palladium chloride in a mixture of hydrochloric acid and methanol) and the second immersion solution (solution of tellurium tetrachloride in acetone) used in Example 1, and left to stand at room temperature for six hours, while the solution was stirred from time to time. After the remaining solution was, then, removed by decantation, the sediment was dried in the air at 120° C. for eight hours, and in a stream of nitrogen at 150° C. for three hours. Then the sediment was reduced by heating at 200° C. for three hours and 400° C. for two hours in the presence of nitrogen saturated with methanol at room temperature, whereby Catalyst I was prepared. The distribution of palladium and tellurium in Catalyst I was examined by repeating the procedures set forth in Example 1. The results are shown in FIG. 10. As is obvious from the results shown in FIG. 10, neither palladium nor tellurium can be distributed evenly throughout the catalyst when they are applied simultaneously in a solution containing a mixture of their compounds, even if an organic solvent is used for preparing the solution.

Catalyst I was tested for the synthesis of 1,4-diacetoxybutene-2, and the results indicated that it was not suitable for practical use because of its low palladium efficiency as shown in the table below.

TABLE 3

| Space time yield (g/lit. cat./hr) | Palladium efficiency (mol/g atom/hr) | 1,4-Selectivity (%) |
| --- | --- | --- |
| 17 | 2.8 | 90.5 |

What is claimed is:

1. A method of preparing a catalyst for synthesizing unsaturated esters, comprising:
   supporting on activated carbon a compound of palladium applied in the form of a solution in an organic solvent containing a mineral acid; then
   supporting on said carrier at least one element selected from the group of tellurium and tin or a compound thereof, applied in the form of a solution in an organic solvent; and
   treating the catalyst so prepared to reduce its metal components.

2. A method according to claim 1 in which said element is tellurium.

3. A method according to claim 1 in which the resulting catalyst contains 0.01 to 10% by weight of palladium and 0.01 to 10% by weight of tellurium, tin or a mixture thereof.

4. A method according to claim 1 in which the organic solvents are oxygenated solvents.

* * * * *